US007141683B2

(12) United States Patent
Haas et al.

(10) Patent No.: US 7,141,683 B2
(45) Date of Patent: Nov. 28, 2006

(54) PROCESS FOR THE EPOXIDATION OF OLEFINS

(75) Inventors: Thomas Haas, Frankfurt (DE); Georg Thiele, Hanau (DE); Gerald Moroff, Liederbach (DE); Norbert Ullrich, Essen (DE); Willi Hofen, Rodenbach (DE); Guido Stochniol, Gelnhausen (DE); Hubertus Eickhoff, Alzenau (DE); Werner Pohl, Essen (DE); Wolfgang Wöll, Maintal (DE); Claudia Brasse, Hanau (DE); José Berges, Schöneck (DE); Percy Kampeis, Dortmund (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 105 days.

(21) Appl. No.: 10/428,607

(22) Filed: May 2, 2003

(65) Prior Publication Data
US 2004/0006239 A1 Jan. 8, 2004

Related U.S. Application Data

(60) Provisional application No. 60/376,845, filed on May 2, 2002.

(51) Int. Cl.
C07D 301/12 (2006.01)
(52) U.S. Cl. .................................................. 549/531
(58) Field of Classification Search ................. 549/531
See application file for complete search history.

(56) References Cited

U.S. PATENT DOCUMENTS

| 2,870,171 | A | 1/1959 | Gable |
| 3,860,662 | A | 1/1975 | Kollar |
| 4,410,501 | A | 10/1983 | Taramasso et al. |
| 4,833,260 | A | 5/1989 | Neri et al. |
| 5,463,090 | A | 10/1995 | Rodriguez et al. |
| 5,523,426 | A | 6/1996 | Jubin, Jr. et al. |
| 5,591,875 | A | 1/1997 | Chang et al. |
| 5,599,955 | A | 2/1997 | Vora et al. |
| 5,620,935 | A | 4/1997 | Thiele |
| 5,675,026 | A | 10/1997 | Thiele |
| 5,760,253 | A | 6/1998 | Danner et al. |
| 5,849,937 | A | 12/1998 | Jubin, Jr. et al. |
| 5,849,938 | A | 12/1998 | Rueter et al. |
| 5,912,367 | A | 6/1999 | Chang |
| 6,042,807 | A | 3/2000 | Faraj |
| 6,063,941 | A | 5/2000 | Gilbeau |
| 6,372,924 | B1 | 4/2002 | Thiele |

FOREIGN PATENT DOCUMENTS

| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 | 2/1984 |
| EP | 0 133 510 A1 | 2/1985 |
| EP | 0 230 349 | 7/1987 |
| EP | 0 230 949 | 8/1987 |
| EP | 0 425 893 A1 | 5/1991 |
| EP | 0 524 816 A | 1/1993 |
| EP | 0 526 945 A1 | 2/1993 |
| EP | 0 560 488 A1 | 9/1993 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 819 683 A1 | 1/1998 |
| EP | 0 827 765 | 3/1998 |
| EP | 0 930 308 | 7/1999 |
| EP | 0 936 219 | 8/1999 |
| EP | 1074547 A1 * | 2/2001 |
| EP | 1 122 248 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 98/47845 | 10/1998 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |
| WO | WO 00/25881 | 5/2000 |
| WO | WO 02/02545 | 1/2002 |

* cited by examiner

Primary Examiner—Taofiq Solola
(74) Attorney, Agent, or Firm—Smith, Gambrell & Russell, LLP

(57) ABSTRACT

A process for the epoxidation of olefins which includes
i) reacting an olefin with hydrogen peroxide in presence of an epoxidation catalyst and an alcoholic solvent;
ii) separating product olefin oxide and unreacted olefin from the reaction product of step i);
iii) recovering a stream comprising the alcoholic solvent; and
iv) subjecting the recovered stream of step iii) to hydrogenation.

31 Claims, No Drawings

PROCESS FOR THE EPOXIDATION OF OLEFINS

REFERENCE TO A RELATED APPLICATION

This application claims the benefit of our provisional patent application 60/376,845 filed May 2, 2002, which is relied on and incorporated herein by reference.

The present invention relates to a process for the epoxidation of olefins, in particular to the working up of the product stream from the epoxidation reaction.

PRIOR ART

From EP-A 100 118 it is known that propene can be converted with hydrogen peroxide into propene oxide if titanium silicalite is used as catalyst. The reaction is preferably carried out in the presence of a water-miscible solvent in order to improve the solubility of propene in the reaction mixture. Preferably solvents are used that have a boiling point between the boiling points of propene oxide and water in order to be able to separate the solvent from the reaction mixture by a distillation stage and recycle it to the reaction. Methanol is preferably used as solvent.

WO-A 99/07690 describes a process for the purification of a methanol-containing product stream from the epoxidation of propene that also contains acetaldehyde as an impurity. In this case the crude product stream from the epoxidation is subjected to a fractional distillation, in which connection it is particularly important that methanol is present in sufficient amount in the overhead product in order to achieve a substantially complete transfer of acetaldehyde to the bottom product. To this end the concentration of methanol in the overhead product is 2–6 wt. %. A distillation column with 20–60 separation stages and a reflux ratio of between 10:1 and 30:1 is furthermore necessary in order to achieve the best possible quantitative separation of the acetaldehyde. This arrangement accordingly involves high investment and operating costs for the distillation column.

From U.S. Pat. No. 5,849,938 it is known that in the distillative working up of the methanol-containing reaction mixture from the propene epoxidation, the difference in volatilities of propene oxide and methanol can be increased by carrying out the distillation as an extractive distillation using water or propylene glycol as extraction agent. The purpose of this extractive distillation is to separate methanol as well as further high boiling point impurities like acetaldehyde as quantitatively as possible from the desired product, namely propene oxide, in one distillation step. The bottom stream from the distillation containing methanol, the polar extraction agent and impurities is preferably further worked-up by distillation to remove the polar extraction agent and the methanol fraction is preferably recycled to the epoxidation stage.

EP-A 1 122 248 discloses a process for the working up of a product stream from the epoxidation of propene that contains propene, propene oxide, methanol and water, by separating this product stream into an overhead product containing propene, propene oxide and methanol, and into a bottom product containing methanol and water, wherein the separation takes place in a pre-evaporator with a maximum of 5 theoretical separation stages and 20 to 60% of the total amount of methanol entrained in the product stream is removed with the overhead product, the residue remaining in the bottom product. From the overhead product propene oxide is separated by extractive distillation using preferably water as extraction agent. The bottom stream from the extractive distillation comprising methanol and water can be directly recycled to the epoxidation stage. From the bottom stream of the pre-evaporation step methanol can be recovered by means of a fractionated distillation and recycled to the epoxidation stage. Although this process has considerable advantages in that the loss of propene oxide by secondary reactions in the working up is significantly reduced, it has now been discovered that in an continuous process whereby methanol recovered from the work-up of the reaction product is recycled to the epoxidation stage in a long term view the activity and selectivity of the catalyst in the epoxidation stage is reduced and a build up of impurities in the propene oxide product is observed.

Therefore it is desired to have a process for the epoxidation of olefins wherein the above discussed disadvantages can be avoided.

In WO 02/02545 the problem of build up of methyl formate in the product propene oxide is addressed. This build up can be reduced if methyl formate is removed from the methanol fraction by fractionated distillation prior to recycling the methanol fraction to the epoxidation stage. This reference is totally silent with respect to the problem of catalyst deactivation and it has been discovered that removing of methyl formate alone in a single distillation step as taught in WO 02/02545 would not solve the problem of long term deactivation of the catalyst system. Especially 1,1-Dimethoxyethan one of the impurities identified to cause catalyst deactivation has a boiling point almost identical with methanol and can therefore practically not be separated from methanol by means of distillation. Furthermore according to the teaching in WO 02/02545 an additional distillation step is necessary and a distillation column having 10 theoretical plates has to be used to achieve desired results contributing to increased investment and process costs.

Therefore it is an object of the present invention to provide a process for the epoxidation of olefins resulting in a recovered solvent stream of increased purity.

SUMMARY OF THE INVENTION

This object has been attained by a process for the epoxidation of olefins by
i) reacting an olefin with hydrogen peroxide in presence of an epoxidation catalyst and an alcoholic solvent;
ii) separating product olefin oxide and unreacted olefin from the reaction product of step i);
iii) recovering a stream comprising the alcoholic solvent, characterized by
iv) subjecting the recovered stream of step iii) to hydrogenation.

Preferably the recovered solvent stream comprises less than 2 wt. % olefin oxide and less than 1 wt. % unreacted olefin, more preferred less than 0.5 wt. % olefin oxide and less than 0.1 wt. % unreacted olefin and is most preferably substantially free of olefin oxide and unreacted olefin to minimize product losses in the hydrogenation step.

According to a preferred embodiment of the present invention the process further comprises the steps of
v) optionally purifying the solvent stream resulting from the hydrogenation step iv) and
vi) reusing the solvent.

Another preferred embodiment of the present invention refers to a process as defined above, wherein the product stream after separation of olefin oxide and unreacted olefin is subjected to hydrogenation and the alcoholic solvent is separated from the hydrogenated stream.

During the investigations leading to the present invention the inventors discovered that not only methyl formate present in the solvent stream recycled to the epoxidation stage may have a detrimental effect on the reactivity of the catalyst system. Also other impurities like carbonyls, acetals and ketals, such as formaldehyde, acetaldehyde, dimethoxymethan and 1,1-dimethoxyethan lead to the deactivation of the catalyst.

The inventors have surprisingly discovered that the level of impurities comprised in the solvent stream recovered from the epoxidation reaction can be substantially lowered by hydrogenation of the recovered solvent stream after the majority of the product olefin oxide and non-converted olefin has been removed from the solvent stream. When recycling the solvent after subjecting to hydrogenation to the epoxidation stage deactivation of the catalyst system can be considerably reduced.

Furthermore it has been discovered, that compounds found as by-products and impurities and that are difficult to separate from the valuable products and additionally lead if the solvent is recycled to a deactivation of the catalyst system, are not only formed in the reaction step, but also in subsequent working-up stages. The formation of undesired by-products and impurities will especially occur in high temperature working-up stages like distillations when peroxide compounds are still present. Peroxides that may occur for example in the product of the epoxidation of propene are hydrogen peroxide and organic peroxides, like 1-hydroperoxy-2-propanol and 2-hydroperoxy-1-propanol that are formed in the reaction stage by the reaction of propene oxide with hydrogen peroxide. Thus an important advantage of the present invention is, that by hydrogenation not only impurities that are difficult to separate are converted into compounds that can be more easily separated but that also reactive intermediates that can result in subsequent reactions to impurities that are difficult to separate are removed.

Thus the present invention is particularly advantageous if the solvent is at least partially recycled to the epoxidation step i), but is not restricted to such an embodiment. Alternatively the solvent recovered from the process of the present invention can also be reused in different manners well known by a person skilled in the art.

DETAILED DESCRIPTION OF THE INVENTION

The process according to the present invention is particularly suitable for the epoxidation of olefins having two to six carbon atoms, propene being particularly preferred. The epoxidation reaction of olefins according to the invention is described hereinafter with the example of propene as preferred olefin.

The epoxidation reaction with hydrogen peroxide is carried out in the presence of a titanium silicalite catalyst in an alcoholic solvent. For the epoxidation of propene a solvent is preferably chosen whose boiling point is between the boiling points of propene oxide and water. Suitable solvents include, lower aliphatic alcohols, for example methanol, ethanol or tert.-butanol. Methanol is preferably used as solvent.

Due to recycling of substances in the process, the solvent used may contain 0 to 20 wt. % of water. Hydrogen peroxide is used as an aqueous solution containing 10 to 70 wt. % of hydrogen peroxide. A hydrogen peroxide crude product obtained from the extraction step of the anthraquinone process and containing 30 to 45 wt. % of hydrogen peroxide is preferably used. Alternatively, hydrogen peroxide solutions in alcohols, preferably in methanol can be used. These alcoholic solutions can be prepared by reaction of hydrogen and oxygen in presence of a noble metal catalyst and the alcohol. Propene may be used mixed with propane in an amount of between 0 and 10 vol. % of propane. Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

In one embodiment of the invention the titanium silicalite catalyst is suspended in the reaction mixture during the reaction. The catalyst is then used in the form of a powder or in the form of a suspendable granular material that has been produced by forming in a manner known per se, for example by spray drying or fluidised bed granulation. When using a suspended catalyst, flow mixing reactors, for example stirred tank reactors or recycle reactors, as well as non-flow mixing reactors, for example tubular flow reactors, may be used for the reaction. A cascade consisting of one to three flow mixing reactors and a non-flow mixing reactor connected downstream is preferably used.

In another embodiment of the invention the titanium silicalite catalyst is used as a fixed bed over which a mixture of the feedstock materials is passed. The catalyst is then used in the form of formed bodies that have been produced in a manner known per se, for example by extrusion with the addition of binders. When using a fixed bed catalyst, reactors with bubble column characteristics can be used, i.e. a continuous liquid phase and a dispersed gaseous phase simultaneously flow through the reactor. Alternatively the reaction can be run in a trickle bed modus.

The epoxidation reaction is carried out at temperatures between 0 and 80° C., preferably between 40 and 65° C., and at elevated pressures of atmospheric pressure to 50 bar preferably 10 to 20 bar under an atmosphere substantially consisting of propene. The propene is used in excess and the residence time in the reactor is chosen so that a hydrogen peroxide conversion of more than 90%, preferably more than 95%, is achieved. The amount of solvent used is preferably chosen so as to achieve a ratio of 1 to 5 parts by weight of solvent to one part by weight of aqueous hydrogen peroxide solution.

Before the working up stage the pressure of the reaction mixture is preferably released in a pressure release stage to the pressure employed in the working up of the propene oxide. Part of the propene dissolved in the reaction mixture and possibly propane is gassed out. The resultant gas is recompressed via a compressor to the pressure prevailing in the reactor and is returned to the reaction. The propene oxide still contained in the gas is preferably recovered by cooling and partial condensation after the compression.

The work-up of the reaction product can be conducted in conventional way such as multiple distillation steps as well know in the art as long as at some stage of the entire working-up procedure at least one solvent stream is recovered. The at least one solvent stream or a combined stream resulting from different stages of the working-up procedure is subjected to a hydrogenation step according to the present invention.

According to a preferred embodiment of the present process in step iv) the recovered solvent stream is subjected to a heterogeneous catalytic hydrogenation at a hydrogen partial pressure of 0.5 to 30 MPa. It is particularly preferred to conduct the hydrogenation step at a temperature in the range of 80° C. and 150° C., preferably 100° C. to 180° C. and at a hydrogen partial pressure of 1 to 25 MPa. Suitable catalysts are selected from supported catalysts comprising one or more of metals selected from the group consisting of Ru, Rh, Pd, Pt, Ag, Ir, Fe, Cu, Ni and Co. Alternatively Raney Nickel and Raney Cobalt both optionally being doped with one or more of the above mentioned can be used. The catalyst support is preferably selected from activated carbon and metal oxides selected from $SiO_2$, $TiO_2$, $ZrO_2$ and $Al_2O_3$, mixed oxides comprising at least two of Si, Al, Ti and Zr and mixtures thereof.

In the epoxidation process of the present invention, carbonyl compounds are formed in the epoxidation reactor or during subsequent working-up stages, especially distillation stages. After separating the product propylene oxide, propene and other light boilers like methylformate from the reaction mixture, a stream comprising most of the solvent methanol, water, residual hydrogen peroxide and carbonyl compounds is obtained.

In addition to the carbonyl compounds and the alcoholic solvent the corresponding acetals and ketals are also present. Therefore, according to a preferred embodiment of the present invention, a hydrogenation system including reactor, catalyst and reaction conditions is chosen to hydrogenate the carbonyl compounds as well as the corresponding acetals, like formals, hemiformals, ketals and hemiketals. These carbonyl compounds can be hydrogenated by using metal catalysts. These metals are preferably Nickel or precious metals. In case of precious metals, the metals are supported.

The catalyst support can be any solid which is inert and does not deteriorate under the reaction conditions. Examples are silica, alumina, titania, zirconia, clays, calcium carbonate or mixed oxides like silica-alumina. Especially suitable catalysts for hydrogenating the carbonyl compounds, acetals and ketals are carbon with precipitated platinum, palladium, iridium or ruthenium. Preferred is ruthenium.

The catalyst support can be in the form of spheres, pellets, tablets, granules, extrudates, balls etc. The precious metal loaded onto the support can be in the range of 0.01 to 50 wt. %. Preferred is the range of 0.1 to 5% based on the weight of the support. The precious metal catalyst can be prepared by any state of the art method. The metal can be distributed over the support surface by reducing the corresponding metal salts. These metal salts can be oxides, chlorides, nitrates, hydroxides, carbonates etc.

These catalysts can be acquired commercially from producers like Degussa or Johnson Matthey (see Johnson Matthey The Catalyst Technical Handbook 2001, page 22 and 23).

Furthermore, to ensure hydrogenation of carbonyl compounds and corresponding acetals and ketals, it is preferred to adjust the temperature in the hydrogenation step to be at least 80° C., more preferably in the range of from 100 to 150° C. and the hydrogen partial pressure to be at least 2 MPa, more preferably in the range of from 3 to 5 MPa. The hydrogenation reactor is preferably operated without additional cooling (adiabatic reactor).

The hydrogenation can be carried out continuously or batch-wise e.g., in a suspension method or a fixed-bed method. It is especially preferred to use a trickle-bed reactor. Such reactors are well known. The fixed-bed catalysts to be used therein are preferably pellets with a diameter of 0.5 to 5 mm, especially 1 to 3 mm and with a length of 1 to 10 mm. The noble-metal content is in the customary range, preferably 0.5 to 5% by weight.

By hydrogenation of a solvent stream resulting for example from the epoxidation of propene with hydrogen peroxide in a methanol solvent, wherein propene oxide and propene have been substantially removed, hydrogen peroxide is converted to water, 1-hydroperoxy-2-propanol, 2-hydroperoxy-1-propanol and hydroxyacetone are converted to 1,2-propanediol, formaldehyde is converted to methanol, acetaldehyde is converted to ethanol and 1,1-dimethoxyethane is converted to methanol and ethanol. Methylformate and dimethoxymethane will under the above specified conditions not be converted or only to a lesser extent.

The alcoholic solvent stream resulting from the hydrogenation step can by either directly reused or if necessary for specific applications additionally purified for example by distillation prior to reusing the alcoholic solvent. After hydrogenation and prior to distillation it is preferred to adjust the pH of the alcoholic solvent stream to be below 7. This can be done by any acid that does not interfere with subsequent process steps like sulfuric acid.

According to the most preferred embodiment the solvent stream purified according to the teaching of the present invention is recycled to the epoxidation stage i) of the present process. Most importantly, in a continuous process deactivation of the epoxidation catalyst can be at least considerably reduced by treating the solvent stream to be recycled in a hydrogenation step. Additionally the build up of low boiling impurities in the propene oxide product that are difficult to remove is substantially reduced resulting in an improved product quality.

Additionally it has been surprisingly found that in a process wherein the solvent for example methanol is recycled to the reaction stage i) a build-up of methylformate and dimethoxymethane is not observed, although these compounds are not or only to a lesser extent converted in the hydrogenation reaction under the above specified conditions. Without wishing to be bound by theory it is believed that hydrogenation removes peroxides which otherwise would react in subsequent working-up stages forming methylformate, dimethoxymethane and precursors to these compounds. At the same time, hydrogenation also removes said and/or other precursors to methylformate and dimethoxymethane, like formaldehyde, and prevents them from being recycled to the reaction stage with the solvent.

Consequently the present invention leads to a more effective and cost-efficient epoxidation process, since the operation cycle between regeneration cycles of the epoxidation catalyst can be considerably prolonged and to an improved product quality. These advantages can be achieved by a relatively simple measure of a hydrogenation step.

Moreover the hydrogenation step can be easily integrated into the work-up procedure of the epoxidation product.

According to one embodiment of the present invention the reaction mixture is separated in a pre-evaporator into an overhead product containing propene, possibly propane, propene oxide and solvent, and into a bottom product containing solvent, water, non-converted hydrogen peroxide higher boiling point by-products, such as for example propylene glycol, and if a suspension method is used for the epoxidation step suspended titanium silicalite catalyst. The pre-evaporator preferably has at most only 5 theoretical separation steps and is designed so that the stripping section corresponds to a simple evaporation and the remaining separation effect is achieved in the rectification section. The pre-evaporator is operated at a reflux ratio of at most 1.5 and if desired may also be operated totally without reflux. The pressure in the pre-evaporator is preferably chosen in the range from 1.5 to 8 bar in order to be able to condense the propene oxide with cooling water from the overhead product without having to use a cooling unit. The pre-evaporator is operated so that between 10 and 60% of the amount of solvent fed in with the reaction mixture is removed with the overhead product and the residue remains in the bottom product. In the operational procedure according to the invention more than 95%, typically more than 98% and preferably more than 99% of the propene oxide fed in is contained in the overhead product, and more than 90%, typically more than 97% and preferably more than 99% of the water fed in is contained in the bottom product. In this embodiment the bottom product from the pre-evaporator is subjected to the hydrogenation step of the present invention.

The product stream fed to the pre-evaporator normally contains 0.5–20 wt. % of propene, 0–4 wt. % of propane, 5–35 wt. % of propene oxide, 35–80 wt. % of methanol, 5–40 wt. % of water, 0.1–8 wt. % of higher boiling point by-products, 0.1 to 5 wt. % hydrogen peroxide and 0–5 wt. % of titanium silicalite catalyst. This product stream is separated in the process according to the invention into an overhead product containing 1–40 wt. % of propene, 0–10 wt. % of propane, 15–75 wt. % of propene oxide, 20–85 wt. % of methanol and 0–5 wt. % of water, and into a bottom product containing 0–2 wt. % of propene oxide, 0–1 wt. % of propene, 30–80 wt. % of methanol, 15–65 wt. % of water, 0.1–10 wt. % of higher boiling point byproducts, 0.1–5 wt. % of hydrogen peroxide and 0–10 wt. % of titanium silicalite catalyst.

The overhead product is preferably only partially condensed and the uncondensed propene, possibly mixed with propane, is recompressed via a compressor to the pressure prevailing in the reaction part and is recycled to the reaction, the propene oxide still contained in the gas preferably being removed by partial condensation after compression. The propene still dissolved in the condensate and possibly propane are stripped out from the condensate in a C3 stripper and the stripped-out gas is recycled to the partial condenser. The mixture of propene oxide and solvent contained in the C3 stripper is separated by distillation into a propene oxide crude product, which can be purified further in a manner known per se, and the solvent, which is recycled to the epoxidation reaction directly or can be combined with other solvent streams from different working-up stages and subjected to hydrogenation prior to recycling the solvent to the reaction stage.

In a particularly preferred embodiment the mixture of propene oxide and solvent, preferably methanol, obtained from the C3 stripper is worked up further by extractive distillation to achieve as quantitative a separation as possible of the solvent. In this connection the mixture of propene oxide and methanol is added to the middle section of an extractive distillation column, preferably at a point corresponding to ⅓ of the total number of theoretical trays counting from the bottom, and a polar solvent with hydroxyl functionality and having a boiling point higher than that of methanol is added to the extractive distillation column at a point above the point at which the condensate enters, preferably at a point corresponding to ⅔ of the total number of theoretical trays counting from the bottom. The propene oxide crude product is distilled off at the head of the column and a mixture of methanol and the polar solvent is extracted as bottom product. The polar solvent is selected from water, glycols, glycol ethers and mixtures thereof. The preferred polar solvent is water since in this case the mixture of water and methanol can be either recycled directly to the reaction step without further purification or preferably is combined with other solvent streams and is hydrogenated prior to recycling.

In order to achieve as complete a separation of the methanol as possible, a column with 25–100 theoretical separation steps and with a reflux ratio of 1–4 is already sufficient on account of the concentration of the propene oxide in the overhead product, the mathematical product of the number of separation steps and the reflux ratio typically being 75 to 125.

On account of the pre-evaporation only a very small reflux ratio for the extractive distillation step is still necessary in order to achieve the desired separation effect. Despite the two-stage procedure the operating costs for separating the water and solvent are thereby reduced compared to the prior art.

A particularly preferred embodiment of the present invention accordingly relates to a process for the catalytic epoxidation of propene in which a) in a reaction step the propene is reacted with aqueous hydrogen peroxide in methanol in the presence of a titanium silicalite catalyst, b) the product stream from the reaction step is optionally passed to a pressure release step, and c) the product stream is then separated, without prior distillative separation, in a pre-evaporator having at most 5 theoretical separation steps into an overhead product containing propene, propene oxide and methanol, and into a bottom product containing methanol and water, 20 to 60% of the total amount of methanol introduced into the product stream being removed with the overhead product and the residue remaining in the bottom product, d) the overhead product from step c) is at least partially condensed, the condensate containing, optionally after stripping out propene and any propane present

| | |
|---|---|
| 0–12 | wt. % propene, |
| 0–5 | wt. % propane, |
| 15–75 | wt. % propene oxide, |
| 25–85 | wt. % methanol and |
| 0–3 | wt. % water, and | e) the condensate from step d) is subjected to an extractive distillation, wherein e1) the condensate is added to a middle section of an extractive distillation column, e2) water is added to the extractive distillation column at a point above the point at which the condensate enters, e3) propene oxide is distilled off at the head of the column, and e4) a bottom product containing methanol and water is removed.

The bottom product from the pre-evaporator is optionally combined with other solvent streams recovered in working-up stages as described above and is subjected to the hydrogenation step of the present invention. The pH of the product resulting from the hydrogenation is adjusted to be below 7 and is then separated in a further distillation step into the solvent, which is returned to the epoxidation reaction, and into a mixture of water and high boiling point byproducts, which is either worked up further or is discharged.

When using a suspended titanium silicalite catalyst the catalyst is recovered from the bottom product of the pre-evaporator by solid/liquid separation, for example by filtration or centrifugation, whereby the solid/liquid separation is carried out prior to the hydrogenation of the solvent stream. A separation of the catalyst at this point of the process is particularly advantageous since the propene oxide, which represents a health hazard, has at this point already been separated and less stringent requirements are therefore placed on industrial safety, which considerably simplifies the overall process and makes it much more cost-effective.

The advantages of the present invention will be apparent in view of the following examples.

COMPARATIVE EXAMPLE

A titanium-silicate catalyst was employed in all examples. The titanium-silicate powder was shaped into 2 mm extrudates using a silica sol as binder in accordance with example 5 in EP-A 1 138 387. The $H_2O_2$ employed was prepared according to the anthraquinone process as a 40 wt-% aqueous solution.

Epoxidation is carried out continuously in a reaction tube of 300 ml volume, a diameter of 10 mm and a length of 4 m. The equipment is furthermore comprised of three containers for liquids and relevant pumps and a liquid separating vessel. The three containers for liquids comprised methanol, the 40% $H_2O_2$ and propene. The 40% $H_2O_2$ was adjusted with ammonia to a pH of 4.5. The reaction temperature is controlled via an aqueous cooling liquid circulating in a cooling jacket whereby the cooling liquid temperature is controlled by a thermostat. The reactor pressure was 25 bar absolute. Mass flow of the feeding pumps was adjusted to result in a propene feed concentration of 21.5 wt-%, a methanol feed concentration of 57 wt-% and an $H_2O_2$ feed concentration of 9.4 wt-%. The reactor was operated in down-flow operation mode.

The cooling jacket temperature was 41° C., the total mass flow was 0.35 kg/h and the maximum temperature was 59° C. Product output was determined by gas chromatography and the $H_2O_2$ conversion by titration. The catalyst selectivity was calculated on the basis of gas chromatographical analysis of the propene oxygenates as the ratio of the amount of propene oxide formed relative to the amount of all propene oxygenates formed. Initial $H_2O_2$ conversion was 96% at a catalyst selectivity of 96%.

The reaction mixture obtained from the reaction after release of pressure was separated in the pre-evaporation stage into an overhead product containing propene, propane, propene oxide and methanol, and a bottom product containing methanol, propylene glycol monomethyl ethers, propylene glycol, water and high boiling point compounds and non-converted hydrogen peroxide. A liquid condensate that contains propene oxide and methanol as well as propene and propane dissolved therein was obtained from the vapour state overhead product. The uncondensed stream, which substantially consisted of propene and propane, was returned to the epoxidation reaction. The propene and propane dissolved in the condensate were stripped from the latter in the C3 stripper and returned in the vapour state together with the stream to the partial condensation stage. The stream, which consisted substantially of propene oxide and methanol and had been freed from propene and propane, was separated in an extractive distillation in which water was fed in as extraction agent immediately underneath the head of the column, into a propene oxide crude product that consisted initially of more than 99.5%, of propene oxide, and into a bottom product that consisted substantially of methanol and water, the water content being less than 20%. The bottom product was returned as solvent to the epoxidation reaction.

The bottom product obtained in the pre-evaporator was separated in a distillation stage at a pressure of 2 bars abs. using a continuously running column having 35 stages at a reflux ratio of 2 for recovering methanol, into an overhead product that consisted of more than 95% of methanol, and into a bottom product consisting of propylene glycol monomethyl ethers, propylene glycol, water, high boiling point compounds and only traces of hydrogen peroxide. The overhead product was continuously returned as solvent to the epoxidation reaction. After 500 h running the epoxidation process the cooling temperature in the reaction step had to be increased to 50° C. to maintain the conversion constant at 95% and the catalyst selectivity dropped to 90%. The propene oxide stream contained 2% acetaldehyde, 0.5% methylformate and 0.2% dimethoxymethane.

EXAMPLE 1

The Comparative Example was repeated with the exception that the bottom product obtained in the pre-evaporator stage was directed to a trickle-bed reactor for continuous hydrogenation. The hydrogenation reactor had an interior volume of 150 ml and was filled with a hydrogenation catalyst in form of extrudates with 2.3 mm diameter comprising 2% Ru on activated carbon (The catalyst was prepared according to the incipient wetness method using $RuCl_3$, "Preparation of Catalyst", Demon, B. et al., Elsevier, Amsterdam, 1976, page 13). The hydrogenation was performed at 140° C. and 40 $bar_{abs}$ at a hydrogen flow rate of 10 ml/h. The hydrogenated product was continuously removed and had a pH of 9. The pH was reduced to be below 7 by adding sulfuric acid prior to entering the final distillation step according to the comparative example.

After 500 h running the epoxidation process the cooling temperature in the reaction step was 42° C. and the $H_2O_2$ conversion was still 96% at a catalyst selectivity of 96%. The propene oxide stream contained 0.07% acetaldehyde, 20 ppm methylformate and 10 ppm dimethoxymethane.

As can be seen from the comparison of both examples the activity of the epoxidation catalyst even after 500 h running the process was only very marginally reduced if the solvent stream was hydrogenated prior to recycling the solvent to the reaction stage. In contrast thereto without hydrogenating the solvent stream a considerable reduction in catalyst performance is observed, which requires a gradual increase in the reaction temperature in order to maintain a constant hydrgen peroxide conversion. The effect on product quality is even more dramatic. Thus it is shown that hydrogenation of the solvent stream to be recycled to the epoxidation process leads to considerably reduced catalyst deactivation and improved product quality.

EXAMPLE 2

The epoxidation reaction was performed as described for the Comparative Example. The bottom product obtained in the pre-evaporation was analyzed and subjected to the hydrogenation as described for Example 1.

The composition of the hydrogenation feed and product are given in Table 1. Apart from hydrogen peroxide, the feed stream was free of other peroxy compounds.

TABLE 1

Hydrogenation, Feed & Product Composition

|  | Hydrogenation Feed [%] | Hydrogenation Product [%] |
|---|---|---|
| Formaldehyde | 0.06 | 0.00 |
| Acetaldehyde | 0.09 | 0.01 |
| Methanol | 72.17 | 71.92 |
| Ethanol | 0.37 | 0.49 |
| 1,2-Dimethoxyethane | 0.54 | 0.59 |
| 1-Methoxypropanol-2 | 0.26 | 0.26 |
| 2-Methoxypropanol-1 | 0.19 | 0.19 |
| 1,2-Propandiol | 0.21 | 0.23 |
| Others | 0.18 | 0.23 |
| Water | 26.19 | 26.60 |
| Hydrogen Peroxide | 0.28 | 0.00 |
| pH | 4.04 | 9.36 |

As is evident from Table 1, by means of hydrogenating the solvent stream, carbonyl compounds like acetaldehyde and formaldehyde are substantially and selectively removed. There is no substantial hydrogenolysis of alcohols like methanol or propandiol. In addition, hydrogen peroxide is completely removed.

The invention claimed is:

1. A process for the epoxidation of olefins comprising
   i) reacting an olefin with hydrogen peroxide in the presence of an epoxidation catalyst and an alcoholic solvent to form a reaction product;
   ii) separating product olefin oxide and unreacted olefin from the reaction product of step i);
   iii) recovering a stream comprising the alcoholic solvent from the reaction product after separation of product olefin oxide and unreacted olefin therefrom;
   iv) subjecting the recovered stream of step iii) to hydrogenation; and
   v) reusing the solvent stream obtained from step iv).

2. The process of claim 1, wherein the solvent stream recovered in step ii) comprises less than 2 wt. % olefin oxide and less than 1 wt. % unreacted olefin.

3. The process of claim 1, wherein the product stream after separation of olefin oxide and unreacted olefin in step ii) is subjected to hydrogenation and the alcoholic solvent is separated from the hydrogenated stream.

4. The process of claim 1, wherein the mixture of product olefin oxide and unreacted olefin separated in step ii) additionally containing the alcoholic solvent is subjected to at least one subsequent working-up step resulting in at least one additional solvent stream and the solvent stream recovered in step iii) is combined with at least one of said additional solvent stream resulting from said at least one subsequent working-up step and the combined solvent stream is subjected to hydrogenation.

5. The process of claim 1, further comprising the steps of
   v) optionally purifying the solvent stream resulting from the hydrogenation step iv) and
   vi) reusing the solvent.

6. The process of claim 5, wherein step v) of purifying the solvent stream comprises
   a) adjusting the pH of the solvent stream resulting from hydrogenation step iv) to be below 7 and
   b) subjecting the stream resulting from step a) to distillation.

7. The process of claim 5, wherein the purified solvent of step v) is at least partially recycled to the epoxidation step i).

8. The process of claim 1, wherein the stream recovered in step iii) comprises carbonyl compounds, acetals and/or ketals as impurities, whereby the level of these impurities is reduced by hydrogenation step iv).

9. The process of claim 8, wherein the stream recovered in step iii) comprises acetaldehyde and acetaldehyde is reduced in hydrogenation step iv) to ethanol.

10. The process of claim 1, wherein in step iv) the recovered solvent stream is subjected to a heterogeneous catalytic hydrogenation at a hydrogen partial pressure of 0.5 to 30 MPa.

11. The process of claim 10, wherein the hydrogenation is operated at a hydrogen partial pressure of at least 2 MPa, and at a temperature of at least 80° C.

12. The process of claim 11, wherein the hydrogenation is operated at a hydrogen partial pressure of 3 to 5 MPa.

13. The process of claim 11, wherein the hydrogenation is operated at a temperature of 100 to 150° C.

14. The process of claim 10, wherein the catalyst is selected from supported catalysts comprising one or more of metals selected from the group consisting of Ru, Rh, Pd, Pt, Ag, Ir, Fe, Cu, Ni and Co, and Raney Nickel and Raney Cobalt both optionally being doped with one or more of metals selected from the group consisting of Ru, Rh, Pd, Pt, Ag, Ir, Fe, Cu, Ni and Co.

15. The process of claim 14, wherein the catalyst support is selected from activated carbon and metal oxides selected from $SiO_2$, $TiO_2$, $ZrO_2$ and $Al_2O_3$, mixed oxides comprising at least two of Si, Al, Ti and Zr and mixtures thereof.

16. The process of claim 14, wherein the hydrogenation is carried out using a fixed bed catalyst in the shape of pellets with a diameter of 0.5 to 5 mm and with a length of 1 to 10 mm.

17. The process of claim 14, wherein the hydrogenation is carried out using a fixed bed catalyst and the recovered solvent stream is directed through the catalyst bed in a trickle mode.

18. The process of claim 14, wherein the hydrogenation is carried out in a hydrogenation reactor without additional cooling.

19. The process of claim 1 wherein the product stream from the reaction step i) contains olefin, olefin oxide, alcoholic solvent, hydrogen peroxide and water, said product stream being separated in a pre-evaporator into an overhead product containing olefin, olefin oxide and alcoholic solvent, and into a bottom product containing alcoholic solvent, hydrogen peroxide and water, wherein 10 to 60% of the total amount of organic solvent introduced with the product stream is removed with the overhead product and the residue remains in the bottom product and whereby the bottom product is subjected to hydrogenation step iv).

20. The process of claim 19, wherein the bottom product of the pre-evaporator is combined with other solvent streams recovered in the process prior to hydrogenation.

21. The process according to claim 19, wherein more than 95%, preferably more than 98% and particularly preferably more than 99% of the entrained olefin oxide is removed with the overhead product, and more than 90%, preferably more than 97% and particularly preferably more than 99% of the entrained water is removed with the bottom product.

22. The process of claim 1, wherein the olefin is selected from a $C_2$–$C_6$ olefin, the catalyst is a titanium silicalite and the solvent is methanol.

23. The process of claim 1, wherein the olefin is propene.

24. The process according to claim 23, wherein the propene is used mixed with propane.

25. The process of claim 24, wherein propane is present in an amount of up to 10 vol. % of propane.

26. The process of claim 19, wherein the olefin is propene, optionally mixed with propane, the catalyst is titanium silicalite and the solvent is methanol.

27. The process of claim 26, wherein the product stream from the reaction step i) contains:

| | |
|---|---|
| 0.5–20 | wt. % propene |
| 0–4 | wt. % propane |
| 5–35 | wt. % propene oxide |
| 35–80 | wt. % methanol |
| 5–40 | wt. % water |
| 0.1–5 | wt. % hydrogen peroxide |
| 0.1–8 | wt. % by-products |
| 0–5 | wt. % titanium silicalite catalyst, | the overhead product from the pre-evaporator contains

| | |
|---|---|
| 1–40 | wt. % propene |
| 0–10 | wt. % propane |
| 15–75 | wt. % propene oxide |
| 20–85 | wt. % methanol |
| 0–5 | wt. % water | and the bottom product from the pre-evaporator contains

| | |
|---|---|
| 0–2 | wt. % propene oxide |
| 30–80 | wt. % methanol |
| 15–65 | wt. % water |
| 0.1–5 | wt. % hydrogen peroxide |
| 0.1–10 | wt. % by-products |
| 0–10 | wt. % titanium silicalite catalyst. |

28. The process of claim 27, wherein the overhead product from the pre-evaporator is at least partially condensed, constituents having a boiling point that is lower than that of propene oxide are optionally stripped from the condensate, and the condensate is then subjected to an extractive distillation using water as extraction agent whereby a head product comprising propene oxide and a bottom stream comprising methanol and water are recovered and the bottom stream is optionally subjected to a hydrogenation step prior to recycling to the reaction step i).

29. The process of claim 27, wherein the titanium silicalite catalyst is present suspended in the reaction mixture and titanium silicalite present in the bottom product from the pre-evaporator is removed by solid/liquid separation prior to subjecting the bottom product to hydrogenation.

30. The process according to claim 1, wherein the epoxidation catalyst is present as a fixed bed.

31. The process according to claim 30, wherein the epoxidation catalyst is an extrudate with a diameter of 1 to 5 mm.

* * * * *